(12) United States Patent
Hughes

(10) Patent No.: US 7,833,182 B2
(45) Date of Patent: Nov. 16, 2010

(54) BACK SUPPORT APPARATUS AND METHOD

(76) Inventor: Phillip K. Hughes, 2038 W. Moccasin Ct., Boise, ID (US) 83703

( * ) Notice: Subject to any disclaimer, the term of this patent is extended or adjusted under 35 U.S.C. 154(b) by 850 days.

(21) Appl. No.: 11/686,221

(22) Filed: Mar. 14, 2007

(65) Prior Publication Data

US 2008/0228121 A1    Sep. 18, 2008

(51) Int. Cl.
  *A61F 5/00* (2006.01)
  *A61F 5/37* (2006.01)
  *A61F 5/02* (2006.01)
  *A61G 15/00* (2006.01)
  *A61B 19/00* (2006.01)

(52) U.S. Cl. .............................. 602/19; 602/5; 128/845; 128/869; 128/874; 2/44; 2/45

(58) Field of Classification Search .......... 602/5, 602/19, 32, 36; 128/869, 874; 424/124; 2/44, 45
See application file for complete search history.

(56) References Cited

U.S. PATENT DOCUMENTS

| | | | | | |
|---|---|---|---|---|---|
| 1,202,861 | A | * | 10/1916 | Kelly | 362/261 |
| 1,371,690 | A | * | 3/1921 | Kelly | 2/44 |
| 1,409,326 | A | * | 3/1922 | Williamson | 2/44 |
| 1,678,584 | A | * | 7/1928 | Branson | 2/44 |
| 3,029,810 | A | * | 4/1962 | Martin | 602/19 |
| 3,570,011 | A | * | 3/1971 | Naig | 2/44 |
| 4,881,528 | A | * | 11/1989 | Scott | 602/32 |
| 5,569,171 | A | | 10/1996 | Muncy | |
| 5,840,051 | A | | 11/1998 | Towsley | |
| 5,951,591 | A | * | 9/1999 | Roberts | 606/241 |
| 6,267,741 | B1 | | 7/2001 | Lerman | |
| 6,776,767 | B2 | | 8/2004 | Reinecke et al. | |
| 6,979,303 | B2 | | 12/2005 | Jestrabek-Hart | |
| 7,553,266 | B2 | * | 6/2009 | Abdoli-Eramaki | 482/124 |
| 2001/0020144 | A1 | | 9/2001 | Heinz et al. | |

(Continued)

*Primary Examiner*—Patricia M Bianco
*Assistant Examiner*—Brandon Jackson
(74) *Attorney, Agent, or Firm*—Pedersen and Company, PLLC; Ken J. Pedersen; Barbara S. Pedersen

(57) ABSTRACT

A device to support the human back/spine and provide assistance in bending, lifting and standing upright comprises a strap and belt system for attachment to the body and one or more bias/tension member to provide the force necessary to urge the user's back to remain or return to a straight position. When used as intended, the device serves to encourage a healthy body position for lifting, and/or to alleviate or prevent back pain associated with bending or lifting. The bias/tension member preferably comprises at least one tension rod that is adjustably fixed to a waist belt, and slidably received by an upper bracket at or near the shoulder blade region of the back. The length of the preferred two tension rods, in effect, may be adjusted by adjusting how or where the rods are fixed to the waist belt, for example. The angle at which the tension rods are held by the upper bracket, and, hence, the angle the upper portions of the tension rods are held relative to the lower portions of the tension rods, may be adjusted to accommodate different body types. With the device installed on the user's upper body, bending over will tend to bend the rods, and, hence, the resilient rods will support or tend to suspend the upper body and will help the user to straighten when desired.

21 Claims, 9 Drawing Sheets

U.S. PATENT DOCUMENTS

| | | |
|---|---|---|
| 2003/0181839 A1 | 9/2003 | Bremer et al. |
| 2004/0077983 A1 | 4/2004 | Reinecke et al. |
| 2004/0082891 A1 | 4/2004 | Daugherty et al. |
| 2005/0038364 A1 | 2/2005 | Vollbrecht et al. |
| 2005/0154337 A1 | 7/2005 | Meyer |
| 2005/0203453 A1 | 9/2005 | Willner et al. |
| 2005/0228325 A1 | 10/2005 | Zours et al. |
| 2005/0245853 A1 | 11/2005 | Scorvo |

* cited by examiner

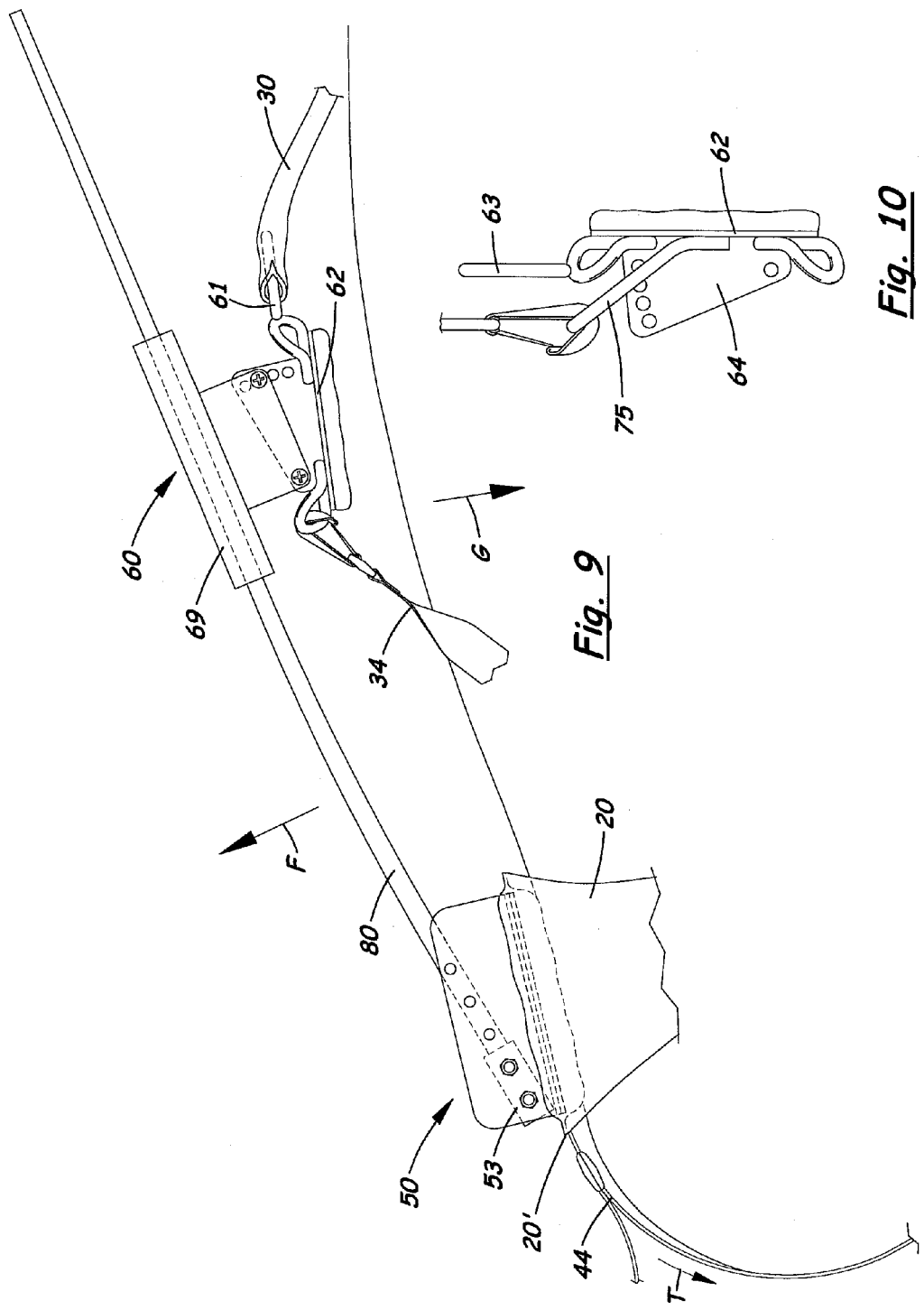

BACK SUPPORT APPARATUS AND METHOD

BACKGROUND OF THE INVENTION

1. Field of the Invention

The present invention relates generally to orthotic appliances used to provide support to the spinal area and related musculature, and more specifically, to devices used to provide support to a previously injured back or to alleviate or prevent back pain resulting from bending or lifting. Embodiments of the invention may be effective for individuals involved in activities or employment requiring bending the upper torso downwardly and/or lifting, wherein the spinal column and related muscles are subjected to stress and pain.

2. Related Art

External devices involving belts, plates, and straps to support or immobilize the human spinal area are well known. Many such belt and plate systems appear in the patent literature, for example:

U.S. Pat. No. 5,840,051, Towsley, discloses a spinal brace formed from a plurality of relatively rigid, hollowed-out parallelepiped portions, adjacent pairs of which are joined along a relatively thin web of flexible material common to the two portions to provide pivotal motion between the two adjacent portions. Relative pivotal movement between the two adjacent portions is selectively restricted by an elongated threaded rod which is pivotally affixed at one end to one of the parallelepiped portions and extends through a portion of the other parallelepiped portion with a nut threadedly engaging the rod adjustment there along to selectively pull the other parallelepiped portion angularly toward the one parallelepiped portion. The nut engages a resilient washer to provide a limited yielding between the portions. The Towsley brace is designed for exterior posterior application to a human patient by a pair of shoulder straps, a waist strap, and forehead and chin straps.

U.S. Pat. No. 6,267,741 B1, Lerman, discloses a cervical thoracic orthosis that includes a chest plate and a back plate with adjustable shoulder straps and waist straps, wherein the chest and back plates each cover nearly all of the user's chest and back, respectively. The device includes an occipital support conforming to the shape of the patient's occipital region, a flexible chin support suspended inside a rigid chin support member, and an upright chin support bar adjustably securing the chin support member to the chest plate.

U.S. Pub. #US 2001/0020144 A1, Heinz, et. al., discloses an orthotic brace that comprises a cable and pulley system for tightening the device around the torso of the wearer. The device may include straps that extend across the shoulders.

U.S. Pub. #US 2004/0077983 A1, Reinecke, et. al.; U.S. Pub. #US 2003/0181839 A1, Bremer, et. al.; U.S. Pat. No. 6,776,767 B2, Reinecke, et. al. disclose devices that may be called waist/torso belts, which brace the back for lifting or bending by wrapping one or more broad belts and/or support plates around the torso. The Reinecke, et al. devices include pistons.

U.S. Pat. No. 5,569,171 (Muncy) discloses a "bi-valve" chiropractic brace that features large, rigid posterior and anterior plates with connecting straps. The device is reported by Muncy to align the lumbar vertebra, to lift the patient's abdominal region, to lock out vertical and lateral rocking motions, and to exert a pelvic tilt to the patient.

U.S. Pub. #US 2005/0154337 A1, Meyer, discloses a thoraco-lumbar spine support/brace for correcting lateral spinal alignment. The brace comprises a frame member defined by two elongate bracing rods extending vertically on opposing (left and right) sides of the wearer that extend generally from the wearer's shoulders to the pelvis. A posterior traction belt extends across the uppermost ends of the bracing rods, at least two anterior traction slings extend across the intermediate portion of the bracing rods, and a pelvic arch extends across the bottom-most ends of the opposing bracing rods. The posterior traction belt, anterior traction slings, and pelvic arch may all be selectively positioned to impart a desired physiological orientation of the wearer's spine.

U.S. Pub. #US 2005/0203453 A1, Willner, et. al., discloses a brace for treatment of low back pain, said brace comprising an anterior abdominal pad and a posterior frame interconnected by connection means including lateral iliac rolls to be positioned at the top of the pelvis bone and straps to be connected to the anterior abdominal pad. The posterior frame has a lumbar pad with pressure setting means for adjusting the applied pressure. The brace is adjustable in magnitude and position of the pressure to correct the curvature of the spine, especially in the lumbar area.

U.S. Pub. #US 2005/0228325 A1, Zours, et al., addresses a spinal brace for relieving the vertebral column in the trunk area between the hips and the thoracic vertebra, comprising a hip clasp supported on the hips of the patient and a thoracic vertebra clasp support on the area of the thoracic vertebra, which are connected by means of rods extending parallel to the vertebral column. The distance between the hip clasp and the thoracic vertebra clasp can be adjusted to adapt to the patient size, by the support rods being changeable in length by being subdivided, into support sections that overlap in the longitudinal direction and can be adjustable fixed to one another in the area of overlapping.

SUMMARY OF THE INVENTION

The present invention comprises a device adapted to provide support to the human back and spinal area, especially during bending and lifting. The invented device is designed and constructed so as to be safely and easily used by an individual, preferably without assistance, to provide support and comfort to the spinal area and to alleviate or prevent back pain and discomfort arising from activities involving bending of the spine and stressing of related muscles in the spinal/back area. The invented device provides forces to the human body that encourage the user to assume the correct posture for lifting; the device encourages the user keep his/her back relatively straight and to maximize use of his/her legs during lifting.

The present invention comprises a chest attachment structure, a waist belt structure, and a biasing mechanism that urges the user to straighten his/her back and that helps support the user's upper body, especially upon bending or lifting. Preferably, the invention also comprises a leg attachment system for anchoring the device to at least one, and preferably both, of the user's legs, for preventing the waist belt structure from tilting or otherwise shifting on the user to a position wherein the device does not offer the desired support and comfort. The preferred biasing system comprises at least one elongated biasing member that runs generally parallel to the spine and that preferably may be adjusted to account for an individual's body type and normal upright posture. Prior to bending or lifting, the device may be worn comfortably and without significant forces on the body, but, upon bending or lifting, the device provides force that resists the user bending over, so that the user is more likely to "lift with his legs" rather than "with his back." Thus, the device tends to support/suspend the user's upper body when he/she does bend over and tends to assist the user in straightening up to an upright position.

The preferred at least one biasing member has one end portion preferably adjustably fixed at or near the waist belt, and an opposing end portion slidably held at a location significantly vertically above the waist belt. The sliding connection of the biasing member(s) allows the biasing member(s) to adjust to the increased circumference of the curved back when the user bends over. Thus, each biasing member is both fixed and moveably connected to the device. The device provides a spring-like suspension for the user's back/spine, rather than a rigid bracing of the back/spine or compression of the torso to the extent of immobilization or difficulty in bending or moving. The preferred embodiments urge the user into the correct "lift with the legs" posture, and/or provide support, suspension, and assistance in lifting/straightening from a bent-over position, while also allowing comfort and a high degree of mobility. Thus, the preferred embodiments provide freedom of movement and comfort until the time when the user needs the force supplied by the device, for example, when he is bending, stretching, or twisting, and the device acts to support and center the back and/or even slightly restrain the user from conducting these movement in a posture or to an extent that might be painful or injure his back.

The preferred embodiments comprise brackets, belts, and straps that secure the rod tension system to the user in the desired position with the at least one rod being spaced from the back of the user, said brackets, belts, and straps being small compared to the large torso plates and torso belts of the prior art. The preferred upper bracket comprises a front portion that may rest on the user's back and a rear portion that connects to said at least one rod to hold it rearwardly spaced out from the user's back. The preferred lower bracket comprises a front portion that connects to the waist belt and a rear portion that connects to said at least one rod to hold it rearwardly spaced out from the user's lower back.

BRIEF DESCRIPTION OF THE DRAWINGS

FIG. 9 is a partial side elevation view of the embodiment of FIGS. 1-8, as it appears when the user is bending over nearly horizontally (with the user's back and hip line running generally from the lower left of the figure to the upper right of the figure).

FIG. 10 is a partial side elevation view of the upper bracket of the embodiment of FIGS. 1-9, which an optional safety line attachment point.

DETAILED DESCRIPTION OF THE PREFERRED EMBODIMENTS

Referring to the Figures, there are shown several, but not the only, embodiments of the invented back brace device used to alleviate or prevent back pain associated with bending and/or lifting, and/or to support the back and spine to help prevent injury.

It will be observed that the preferred back brace appliance 100 is fastened to the wearer utilizing three attachment systems, comprising, at an upper portion of the invented device, a chest attachment system 12; at a mid-portion, a belt structure 14 to be worn around the waist and/or to ride on the hips; and, at a lower portion, a strap system 16 to be attached about the upper legs. All of the aforementioned attachment means are fully adjustable to suit the size and shape of the user, utilizing conventional strap buckling and adjustment means, such as buckles, hook and loop fasteners, slidable fasteners, ties, hooks, snaps, latches, or other adjustable connectors or adjustable-length straps, belts, or ties.

Figure 2:
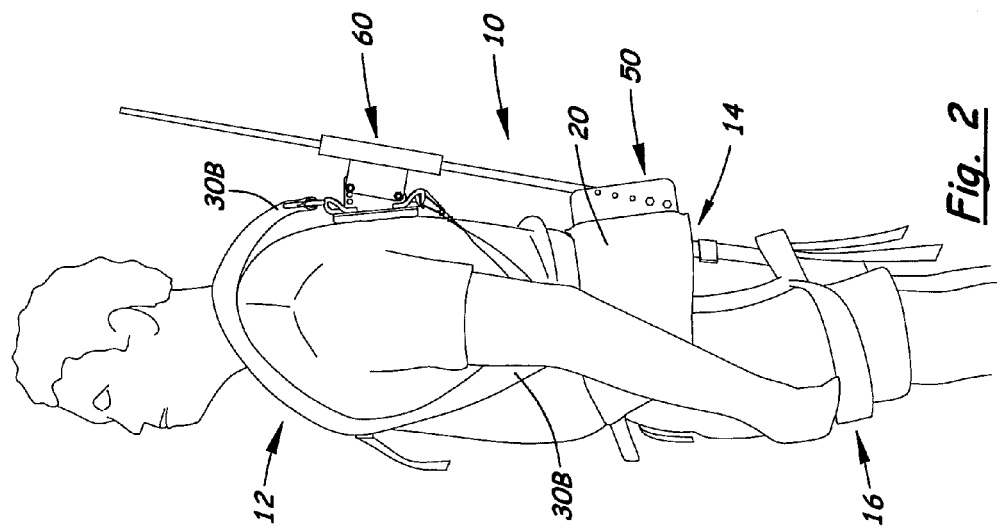
FIG. 2 is a side elevation view of the embodiment of FIG. 1.
Figure 1:
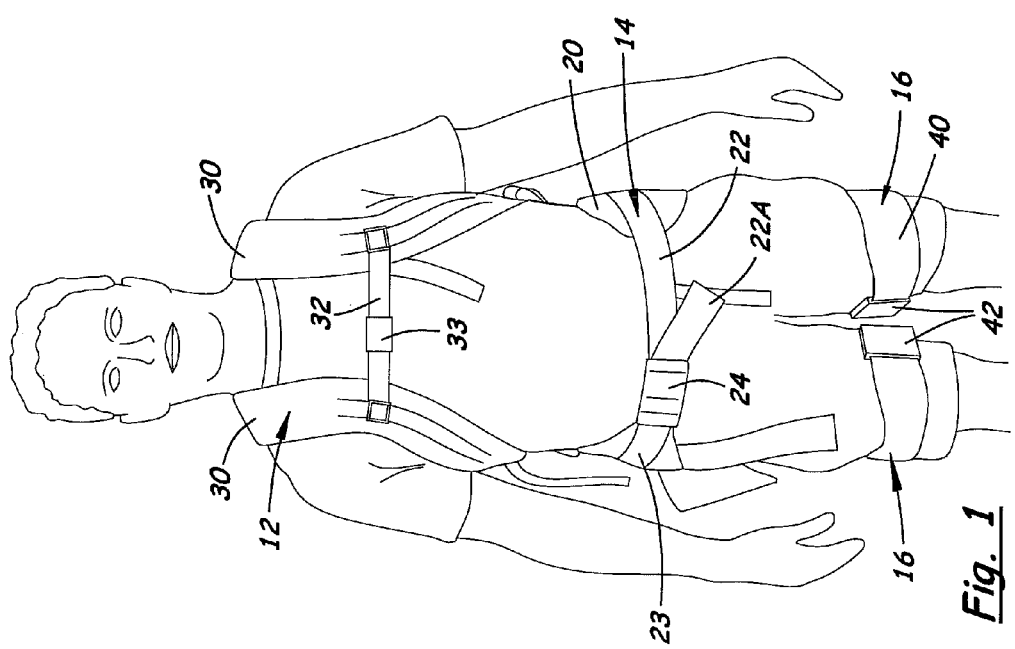
FIG. 1 is a front elevation view of one embodiment of the invented back brace, being worn by a user.
Figure 3:
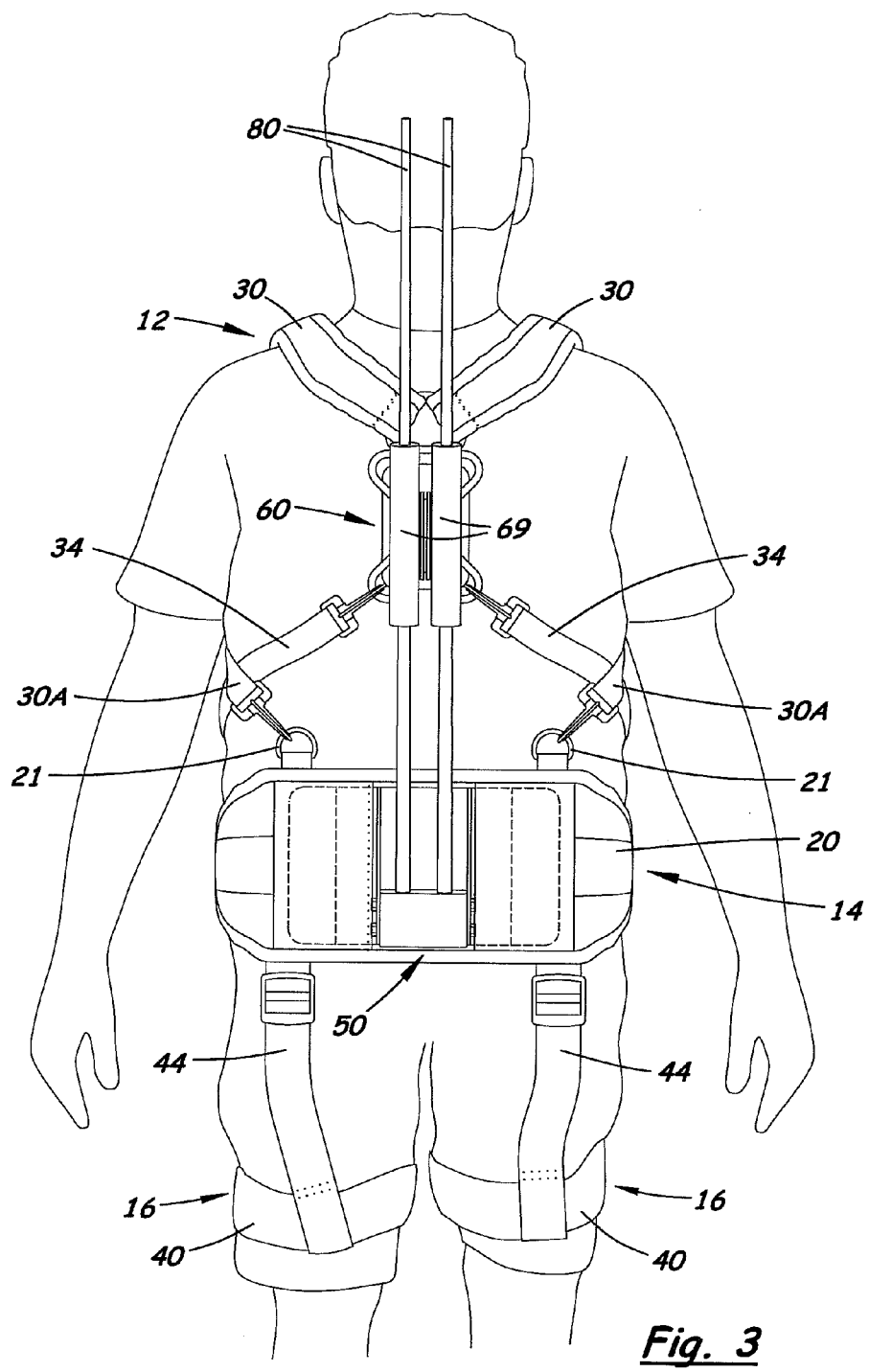
FIG. 3 is a rear elevation view according of the embodiment of FIGS. 1 and 2.
Figure 4:
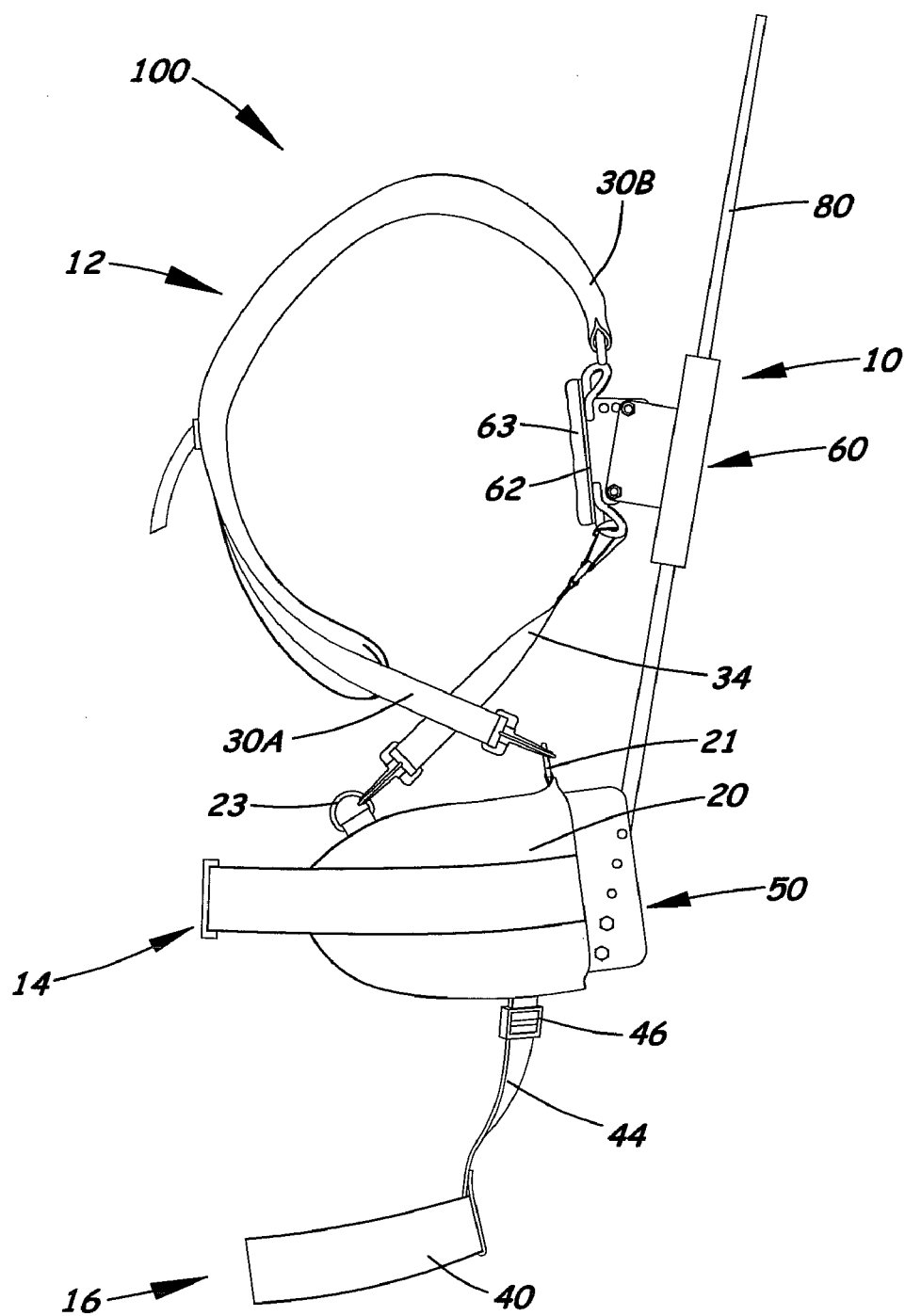
FIG. 4 is a side elevation view of the embodiment of FIGS. 1-3, generally in the configuration that it assumes during use, but without showing the body of the user.
Figure 8:
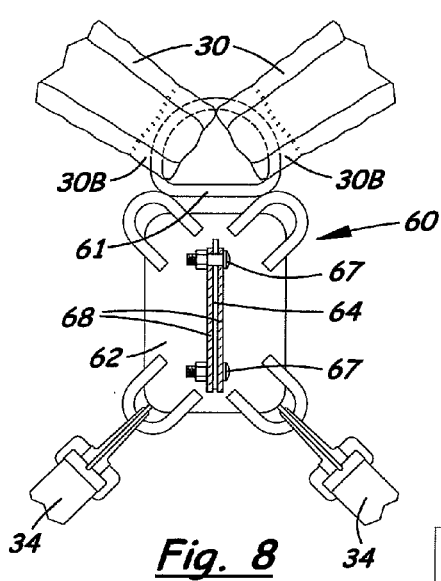
FIG. 8 is a partial plan view of the shoulder unit or "upper bracket" of the embodiment of FIGS. 1-7, viewed along the line 8-8 in FIG. 5.

Referring especially to FIGS. 1-3, one may see that waist belt assembly 14 is comprised of padded belt 20, straps 22 and 23, and buckling and adjustment means 24. In use, waist belt 20 is placed and secured around the waist, and may rest on the hips, of the user. Straps 22 and 23, fixed to the ends of waist belt 20, may be connected by means of buckle 24 or other attachment means such as discussed above. Adjustment for correct fit may be accomplished, for example, by pulling to the user's left on strap 22 at end 22A in FIG. 1.

Figure 6:
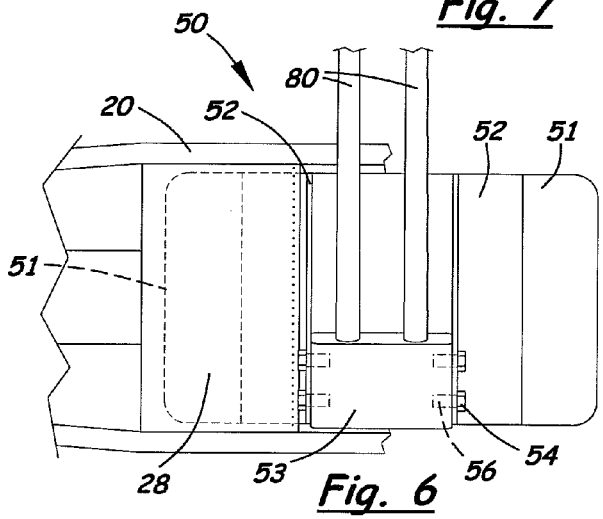
FIG. 6 is a partial rear elevation view of the hip/waist unit or "lower bracket" of the embodiment of FIGS. 1-5, viewed along the line 6-6 in FIG. 5.
Figure 5:
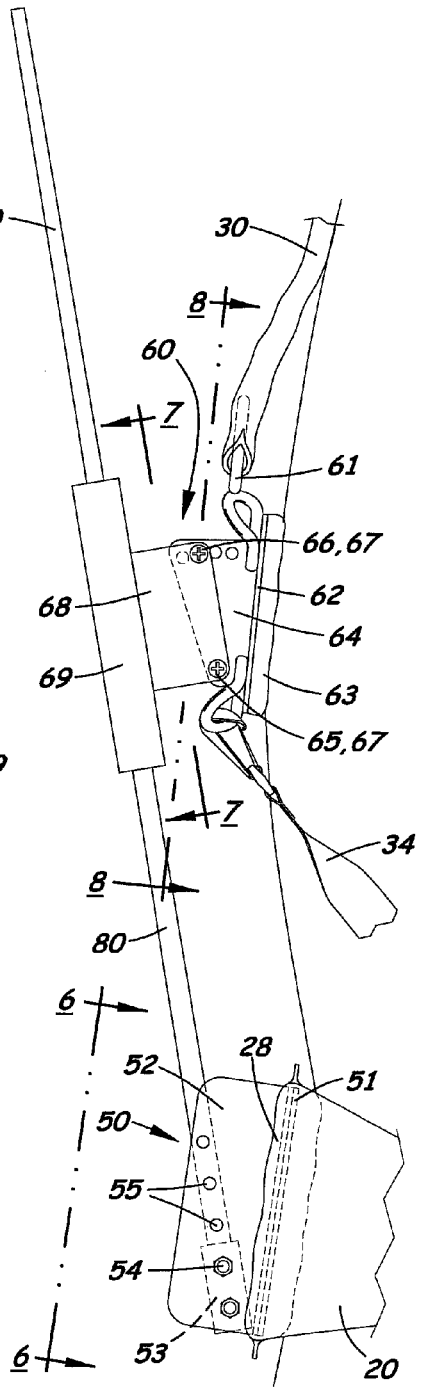
FIG. 5 is a partial side elevation view of the back portion of the embodiment of FIGS. 1-4 (generally, the device without the shoulder, waist, or leg belts shown).

Referring especially to FIGS. 5-6, a lower bracket assembly 50 is provided on a posterior portion of the waist belt and receives the lower region(s) of the preferred tension rod(s) 80. This may be accomplished by a front portion of the lower bracket assembly 50 being connected to the waist belt 20 and a rear portion of the lower bracket assembly 50 extending rearward away from the user to connect to the lower region(s) of the preferred tension rod(s) 80. Thus, the lower bracket assembly is one embodiment of what may be called a posterior bracket assembly.

Shown to best advantage in FIGS. 1-4, 5, and 8 is chest strap assembly 12, wherein straps 30 are worn over the shoulders and extend downwardly along the torso to make connection at ends 30A with waist belt 20 at rings 21 provided therefore. Chest straps 30 are connected to the upper bracket assembly 60, preferably by straps 30 being permanently connected at their ends 30B to ring 63, which ring 63 is preferably permanently connected to back plate 62. With the invented back brace system properly installed upon the body and with the body in an upright attitude, back plate 62 with attached pad 63 rests comfortably against the center of the back, generally between and typically slightly below the shoulder blades, making the upper bracket assembly one embodiment of what may be called a posterior bracket assembly. A connection portion (discussed in more detail later in this Detailed Description) extends rearward from the back plate 62 to connect to the preferred tension rod(s).

Lateral chest strap 32, using buckling and adjustment means 33, is connectedly mounted between chest straps 30 and serves to keep chest straps 30 properly situated upon and around the left and right portions of the chest. Side straps 34 are positioned between and connected to back plate 62 at ends 34A and to waist belt 20 at ends 34B utilizing rings 23 provided therefore.

Typically, the user will don the chest strap assembly 12 first, followed by the waist belt assembly 14, in a way similar to donning a jacket and then buckling the belt of the jacket, for example. Then, the user will typically fasten leg strap assemblies 16. Leg strap assemblies 16 extend down from the waist belt assembly 14 for securement about the upper legs. Leg strap assemblies 16 are comprised of straps 40 fitted around each leg and secured with buckles 42 or other buckling or adjustment means, such as discussed above in the second paragraph of this Detailed Description. Attached at the lower rear portion of waist belt 20 and extending downwardly along the buttocks to make connection with leg straps 40 are buttock straps 44, adjusted snugly along the buttocks utilizing adjustment means 46.

Preferably, the leg strap assemblies 16 maintain the proper position of waist belt 20 on the waist of the user regardless of the attitude of the back of the user; the leg strap assemblies 16 provide downward and inward (against the body) force counteracting forces working to tilt or otherwise shift the waist belt 20 on the user's torso. When leg straps 40 are secured properly about the upper legs and buttock straps 44 are secured snugly between waist belt 20 and leg straps 40, waist belt 20 is maintained around the waste in a more or less permanent position, wherein the rear portion of the waist belt 20 is parallel, and close, to the plane of the lower back. When the user bends over, if not for the counteracting forces of the leg strap assemblies 16, approximately the rear half of the waist belt would tilt out of being parallel and close to the plane of the lower back (lower edge of the belt 20 moving outward from the user's body) in response to the bias of the tension rods 80. This may be understood by viewing FIGS. 9, 9A, and 11, wherein it may be imagined that, without the force T provided by the straps 44, the lower ends of tension rods 80 would pivot/tilt the waist belt 20 lower edge 20' away from the user, in effect, reducing or eliminating the beneficial back straightening and supporting force of the tension rods. In other words, preferably, the waist belt does not significantly move on the human body even when the user bends over, and this has been found by the inventor to be important for the preferred tensioning system 10 to operate as intended. By maintaining the proper position of waist belt 20 on the user, the leg strap assemblies 16 help maintain the ability of the tension rod system (described in more detail below) to suspend and support the user's upper body when the user bends over.

Figure 9A:
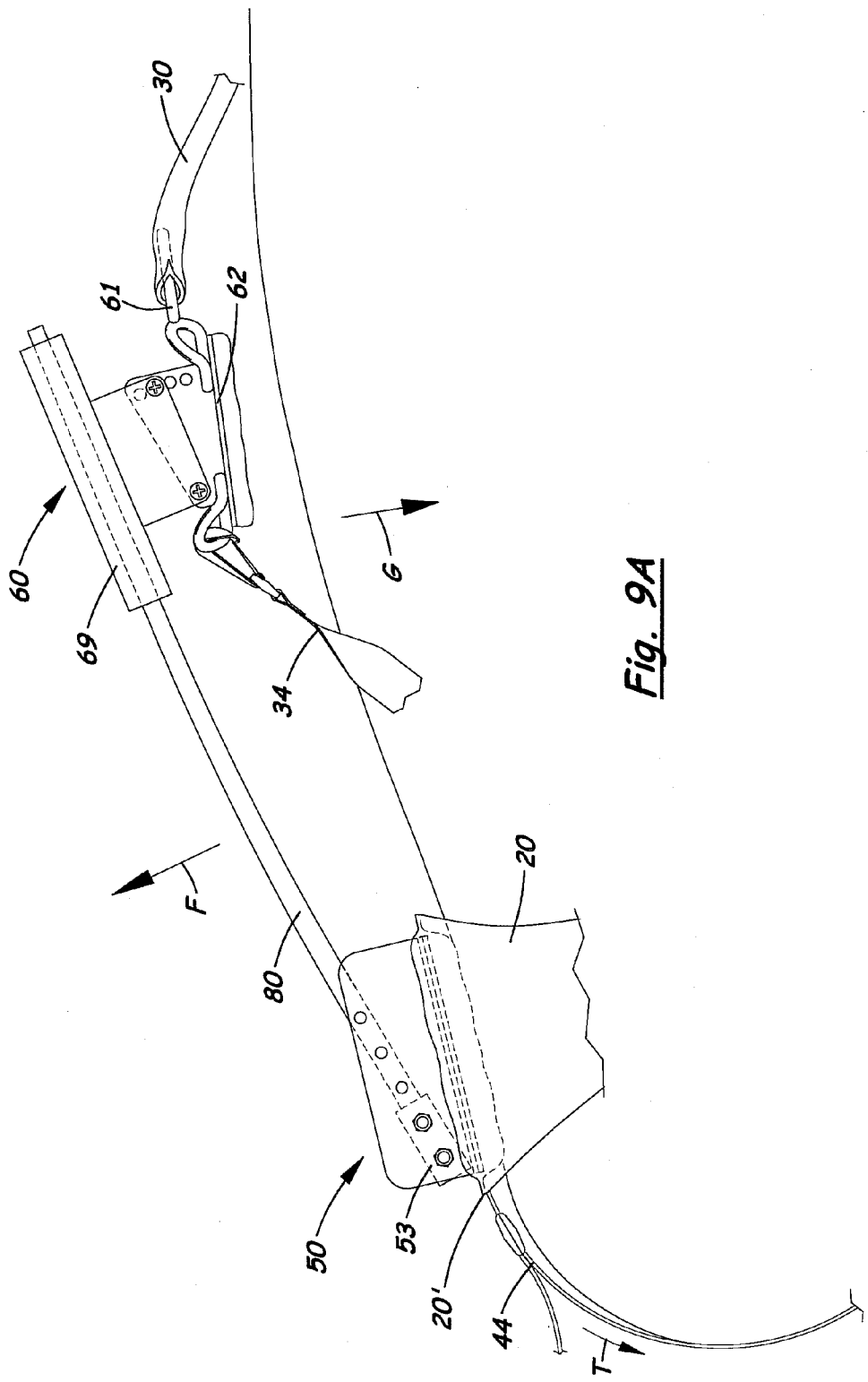
FIG. 9A is a partial side elevation view of an alternative embodiment of the invention, wherein the tension rods are shortened to the extent that they extend out only slightly from the tension rod tubes when the user bends over.

The following discussion further details the preferred tensioning system 10, which is shown to best advantage in FIGS. 5-9, 9A, and 11. Tensioning system 10 comprises lower bracket assembly 50 (detailed in FIGS. 5 and 6) and upper bracket assembly 60 (detailed in FIGS. 5, 7 and 8) cooperating with tensioning rods 80 (shown to best advantage in FIGS. 5, 9, 9A, and 11). The difference between FIGS. 9 and 9A is that FIG. 9A features tension rods that are much shorter than those in FIG. 9, for example, about 2½ feet long in FIG. 9A rather than about 3½ feet long in FIG. 9. Preferably, the tension rods 80 only need to be long enough to extend from the lower bracket assembly 50 to the upper bracket assembly 60, and to slide within the tension rod tubes (without sliding out) to the full extent that is required by the particular user's full range of bending. Typically, the tension rods will slide a distance in the range of 4-8 inches relative to the upper bracket assembly to accommodate said user's full range of bending. FIG. 9A illustrates a tension rod version that places the upper ends of the tension rods just slightly outside of the tension rod tubes (for example, about 1 inch) when the user has bent over a significant amount. Theoretically, the tension rod ends could be inside (but not extending out from and not falling out of) the tension rod tubes when the user bends over to his/her full extent, but this is less desirable due to the increased chance that the rod ends may become stuck or bound-up inside the tubes.

Lower bracket assembly 50, provided in or on the waist belt 20, is comprised of support plate 51, to which are preferably permanently attached angle members 52, arranged upon support plate 51 as shown, the perpendicular walls of said angle members being spaced apart accordingly to receive block 53, within which are preferably permanently mounted the lower ends of tensioning rods 80. The location of block 53 may be adjusted upwardly or downwardly within angles 52, utilizing the multitude of adjustment holes 55 provided within angle members 52. Proper positioning of block 53 having been attained for a particular user, threaded fasteners 54 are inserted through holes 55 and into corresponding threaded holes 56 within block 53, thereby fixing the position of block 53 within angle members 52. The front portion of lower support structure 50 is preferably secured within waist belt 20, for example, wherein support plate 51 resides within pockets 28 that are a part of the fabric structure of the rear outer portion of waist belt 20. Alternative systems may be used for providing an adjustable connection between the tension rods and the waist belt, for example, pins, clips, or other fasteners adjustably connecting the rods themselves to the belt, or adjustably connecting a rod holder (to which the rods might be fixed) to the belt. Alternatively, the tension rods may be fixed without adjustment means to the waist belt or to a bracket or assembly provided on the belt.

Note that the support plate 51 is a small plate of the lower bracket assembly 50 that, as it is attached to the waist belt, rests with the waist belt against the user's lower back. Note also that this small plate 51 does not cover a substantial portion of the user's back, and, instead, extends vertically only along a few inches (preferably 4-8 inches long) of the lower spine area and preferably is only about 2-5 inches wide. Thus, neither the plate 51 nor the lower bracket assembly 50 is adapted to be a significant or sole support member, compression member, or immobilizing member for the back/spine, but rather the lower bracket assembly and its parts (such as plate 51) connect the preferred tension rod(s) to the rest of the back brace assembly 100. Note also that the preferred plate 51 and the entire preferred lower bracket 50 take up (cover or contact) a very small portion of the lower back/lower spine area, and may be said to be located on the lower back and preferably to extend vertically over only about ¼-⅕ of the length of the spine.

The role of preferred upper bracket assembly 60 in its cooperation with preferred tension rods 80 may be described as follows. Upper bracket assembly 60 is comprised of back plate 62 upon the inner surface of which is affixed pad 63 which rests against the back of the user (typically over the clothing of the user). Protruding outwardly from and perpendicular to back plate 62 is plate 64 containing pivot hole 65 and adjustment holes 66. Tension rod tubes 69 and associated brackets 68 are assembled, for example by welding or by plastic molding of the parts, such that brackets 68 permit a space between them sufficient to allow the insertion of plate 64. This having been accomplished, fasteners 67 are used to secure brackets 68 to plate 64 at pivot hole 65 and also at any one of a plurality of adjustment holes 66. It will be observed that, with the use of pivot hole 65 and adjustment holes 66, a rotational adjustment system is provided for the tension rods 80. Said rotational adjustment system may be used to adjust the resting position of the rods (before the user bends over) relative to the upper bracket assembly, in view of the different body shapes and forms of the user. The relationship/location of the upper bracket assembly relative to the lower bracket assembly may be different for different users, and the rotational adjustment system may be used to compensate for this to provide a correct fit for said different users, preferably so that the tension rods are "just shy" of being tensioned (not quite tensioned/bent) when the user is standing in a comfortable, upright posture.

The tension placed on the tension rods 80, upon the user bending, is preferably tension of bending the rods rather than stretching them. The rods 80 are of such material, size and shape that they resiliently return to being straight when possible; this tendency to return to straight produces force that works to keep the wearer's back straight, or, importantly, works to support/suspend the upper body of the wearer when he does bend over, and works to lift the wearer and help him straighten his back when he is wishes to stop bending over.

Note that the back plate 62 is a small plate of the upper bracket assembly 60 that, during most or all periods of use of the back brace appliance 100, rests against the user's back generally between, and somewhat below, the user's shoulder blades. Note also that this small plate 62 does not cover a substantial portion of the user's back, and, instead, preferably extends vertically only along a few inches (preferably 4-8 inches long) of the spine area and preferably is no wider than the distance between the shoulder blades (preferably 2-5 inches wide). Thus, neither the preferred back plate 62 nor the preferred upper bracket assembly 60 is adapted to be a significant or sole support member, compression member, or immobilizing member for the back/spine, but rather the upper bracket connects the preferred tension rod(s) to the rest of the back brace assembly 100. Note also that the back plate 62 and the entire upper bracket assembly 60 take up (cover or contact) a very small portion of the back/spine area, and may be said to be centrally located on the back and preferably to extend vertically over only about ¼-⅕ of the length of the spine. As the upper bracket assembly 60 is not intended to itself to provide significant or sole support, reinforcement, or compression of the back/spine or torso, an upper bracket 60 that has a small contact area (small "footprint") on the back is desired, as this increases comfort and freedom of movement for the user. The cooperation of upper bracket assembly 60 with tension rods 80 is discussed later in this Detailed Description.

Figure 7:
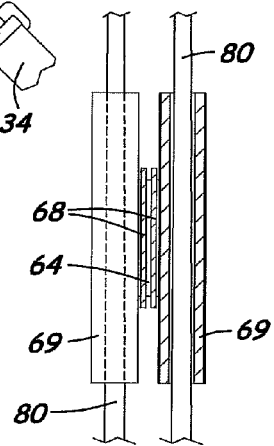
FIG. 7 is a cross-sectional partial elevation view of the tension rod slide system of the embodiment of FIGS. 1-6, viewed along the line 7-7 in FIG. 5.

Referring especially to FIG. 7, it will be observed that tension rods 80 are free to slide longitudinally in upper bracket assembly 60, preferably by means of sliding longitudinally within rod tubes 69, as the attitude of the body changes from upright to bent-over, or any position in between. The rods 80 sliding through the rod tubes 69 allows the rod tubes to apply significant force in a transverse direction (radial, perpendicular to the length of the rods) to the rods, but little axial force. (Note that, as discussed later, that there may be some axial force by the tubes 69 on the rods, which, if unopposed, may encourage the waist belt to "ride up" on the user's back). The transverse force works to bend the rods further than they have been in their pre-tensioned condition. Depending upon the extent of pre-tensioning of the rods, the rods may be difficult to bend further, which translates into a substantial force being produced by the rods that works to keep the wearer's back substantially straight, and/or a substantial force supporting the wearer when he does bend over and lifting the wearer to help him straighten his back when he wants to straighten up.

Figure 11:
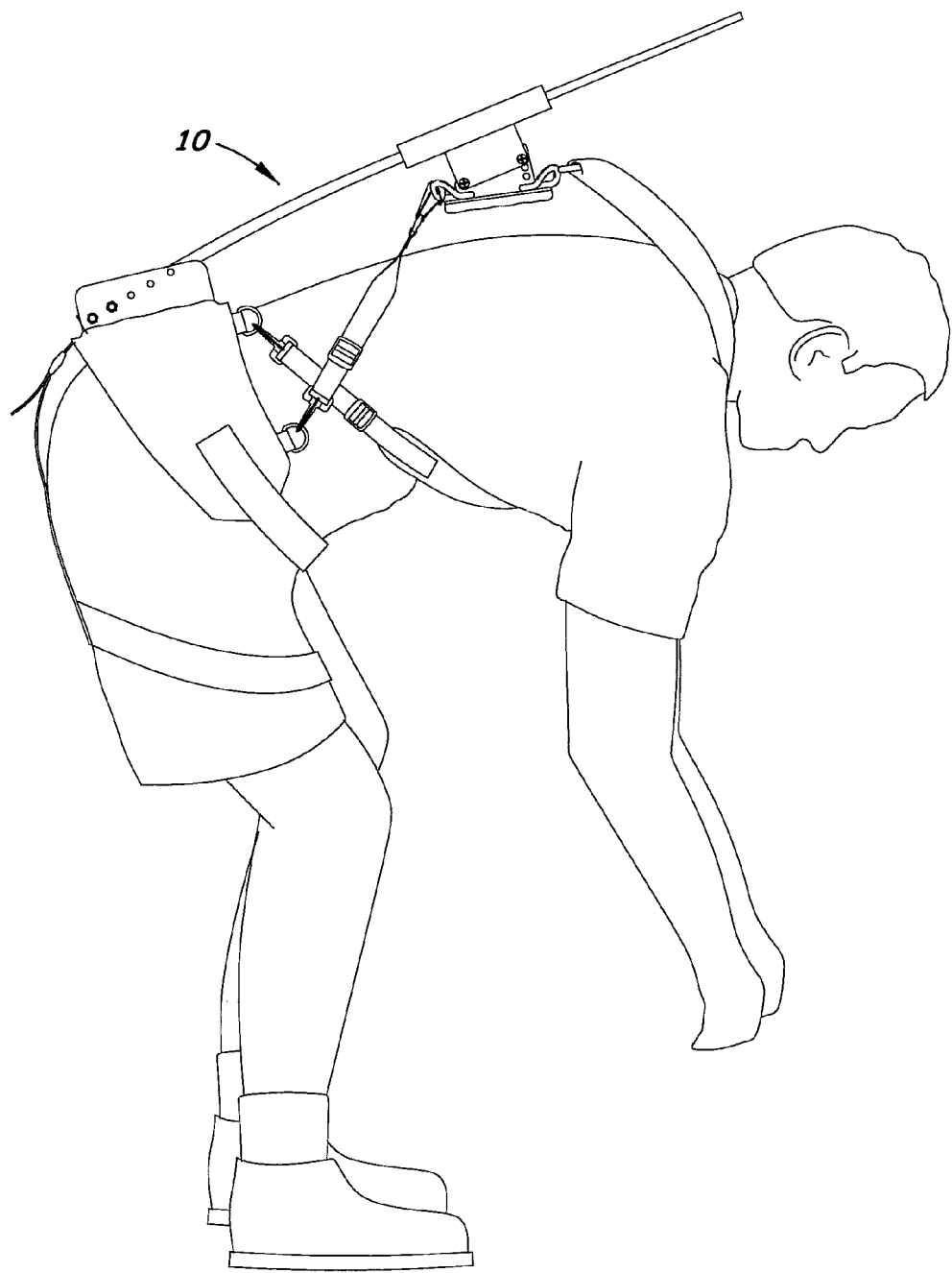
FIG. 11 is a side view of a user, wearing the embodiment of FIGS. 1-9, bending over.

Referring especially to FIGS. 9 and 9A, the back and buttocks are shown with the user of the device in a bent over position (curved line extending from lower left edge of FIGS. 9 and 9A and up slightly as the line extends to right edge of FIGS. 9 and 9A). FIG. 11 shows the device in use, with the entire body of the bent-over user being shown. Waist belt 20 and attached lower bracket assembly 50 are held in a fixed or substantially fixed position on the wearer by tension, represented by arrow T, exerted by buttock straps 44 attached to waist belt 20. Note that, if not for the legs straps system 16 and the buttock straps 44 connecting the legs straps system 16 to the waist belt 20, the wearer's bending over would tend to tilt the waist belt 20 (especially, lifting the lower edge 20' away from the wearer's back) rather than bending the tension rods. Note also, in FIGS. 9 and 9A, that the upper bracket assembly is slightly lifted off of the user's back, due to the forces placed upon it by the tension rods.

With the waist belt 20 and lower bracket assembly 50 completely or substantially fixed in place relative to the wearer's back (not tilting relative to the back), it will be observed that, as a person bends at the waist and the torso moves downwardly, upper bracket 60 moves relative to the lower bracket assembly 50, thus sliding along and also bending the tension rods 80 to assume a more curved shape than they were when the user is standing upright. The curve, and therefore the bending tension, increases in tension rods 80 the more the upper torso is moved downwardly. Again, as noted above, this tension is preferably substantially or entirely from bending and not from stretching or axially pulling the rods. The tension so-created in tension rods 80 lends added support to the back in the bent-over attitude of the body, as indicated by the force arrow F in FIGS. 9 and 9A that opposes the force of gravity, represented by arrow G. To the extent that the wearer is actually using his/her own muscles to force himself into the bent-over attitude, the force F of the rods 80 will also work to oppose that force. When the user of the invented device desires to return to an upright position, the tension present in rods 80, exerting upward force F opposing the force of gravity G, assists the user to return to an upright position without relying solely upon the muscles of the back to do so.

Referring now to FIG. 10, it will be seen that a suitably strong ring 75 may be attached to back plate 62, to which a safety cable may be attached when a user is working in an environment where such a cable is required, for example, construction work many feet above the ground. With chest attachment system 12, waist belt structure 14, and leg strap system 16, and their associated buckles or connections made sufficiently strong, the device 100 may act as a body harness for improving worker stability and safety in precarious places and/or for meeting OSHA requirements for safety harnesses/ lines in said working conditions.

Figure 12:
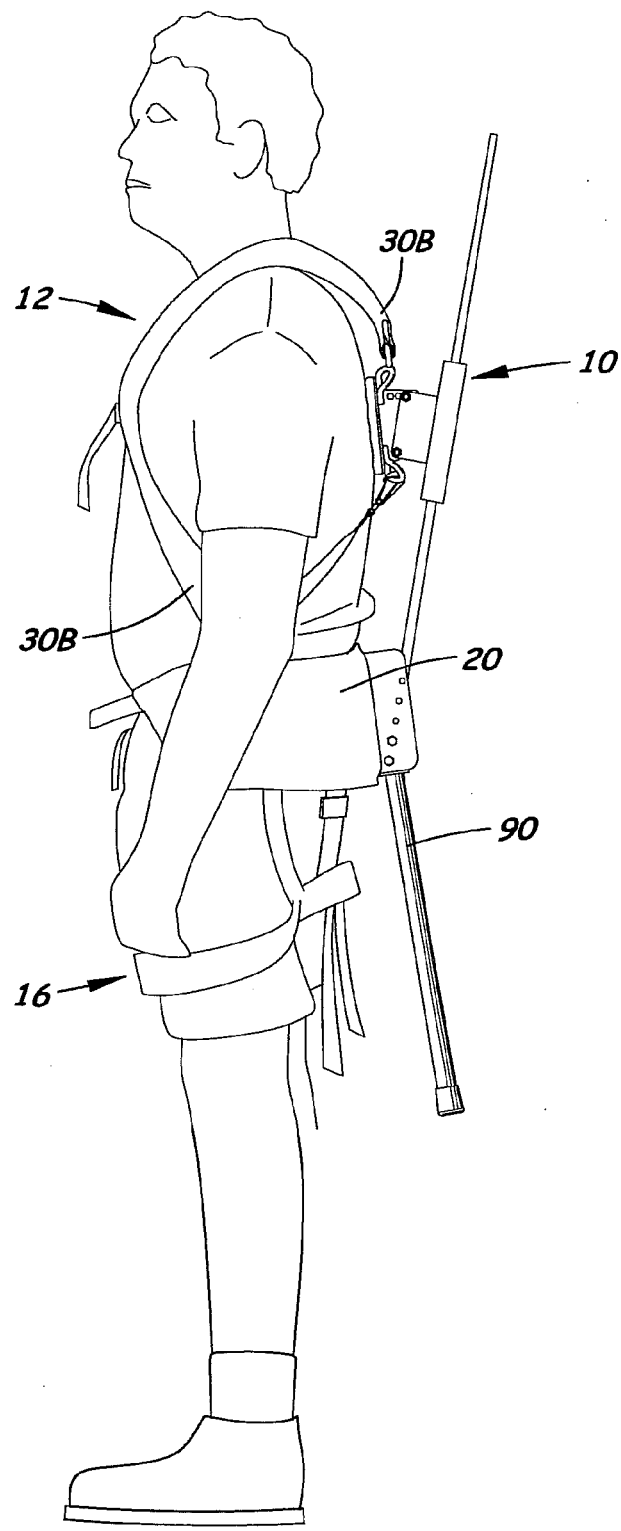
FIGS. 12 and 12A illustrate alternative embodiments of the invented back brace that comprise a sitting support extending down from the waist belt/lower bracket.
Figure 12A:
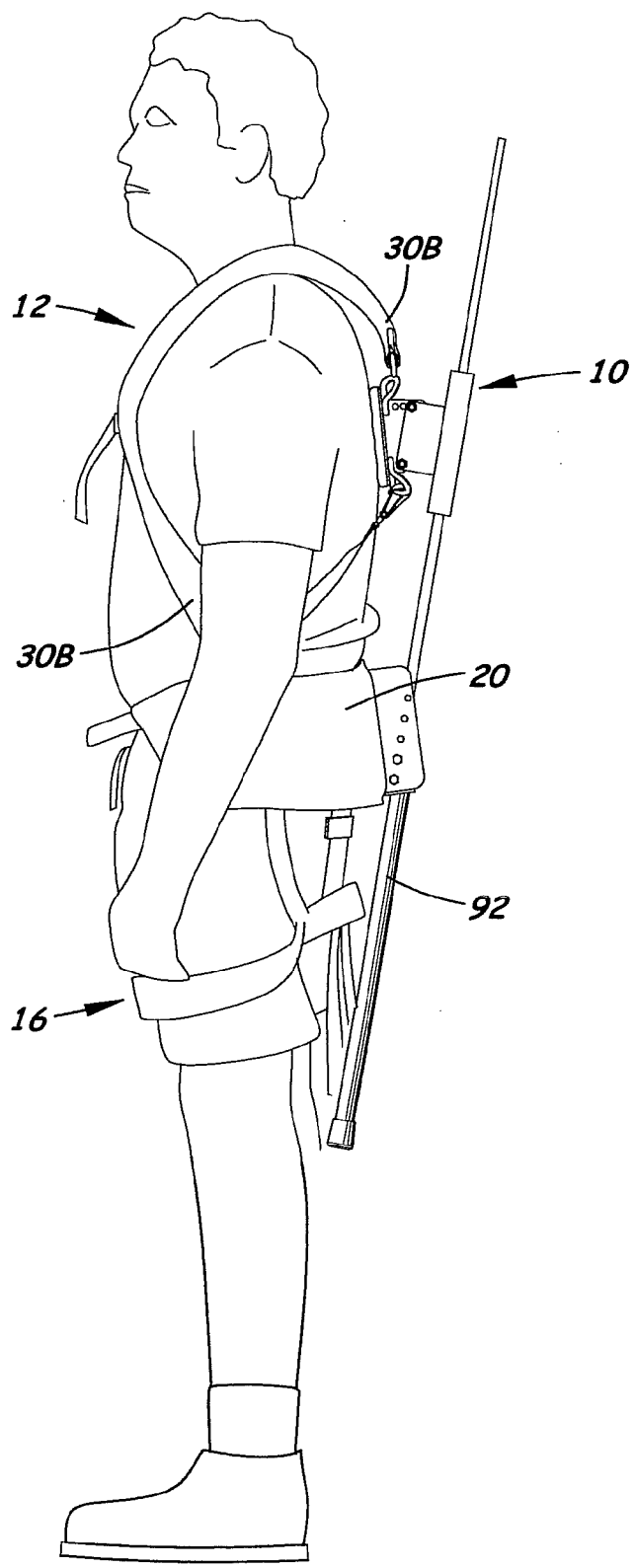

FIGS. 12 and 12A illustrate two of many possible embodiments that include a seat or prop member extending downward below the waist belt. Such a seat or prop member may be used when the user of the device kneels down or otherwise bends his knees and body to an extent wherein he could comfortably sit or lean backward on said seat or prop member. In FIGS. 12 and 12A, a rigid, elongated prop member 90, 92 extends downward from the lower bracket assembly, and, hence, generally from the waist belt 20, to about calf level on the user when he is standing up. When the user sits or crouches, he may lean back, or actually sit, on the prop member 90, 92 to rest or stabilize his position or posture. In FIG. 12, prop member 90 lies generally parallel to the user's legs, which may place it at an obtuse angle of about 150-170 to the tension rods 80. In FIG. 12A, prop member 92 lies generally parallel to the tension rods 80, so that the prop member 92 is slants slightly inward toward the user's legs. Both prop members 90, 92 are preferably single posts, with a rubber cap 93, wherein the bottom end of the prop members 90, 92 is centered behind and between the user's legs so that said bottom end becomes the contact with the ground or floor. These examples illustrate two of various orientations and angles of possible seat/prop members, as many may be designed for different preferences, body styles, and work environments. The elongated prop member 90, 92 illustrates only one shape and length of many possible seat/prop members, and, alternatively, the seat/prop may be made broader, of different shapes, and/or may be adjustable in length or angle relative to the waist belt, tension rods, and/or user's body. Preferably, the seat/prop member or members are not of such design that they would easily hook onto other objects, to help ensure safe use of the device.

Optionally, loops, pouches, holsters, pockets, and/or other holders for tools or personal items may be included on the device. For example, embodiments of the device may be modified for adaptation to various different jobs or crafts, by including particular types and sizes of loops, pouches, holsters, pockets, or holders on the waist belt, chest belt, or leg belt systems. Thus, due to the linkage between the chest strap system and the waist belt system (by straps 30, 30A and 34, for example), the weight of tools or equipment may be born at least in part by the shoulder straps even when hung from the waist belt.

The preferred embodiment may be said to include at least one bias member or tension member that extends along a substantial length of the wearer's back but is distanced from the wearer, and even the wearer's clothing, in order to prevent the at least one bias member from rubbing on the back of the user. The at least one bias member is preferably connected to straps, belts, or harness only at a lower location at or near the lower back (near the user's waist) and at an upper location at or slightly below the region below the shoulder blades. The upper bracket assembly is preferably configured to hold said at least one bias/tension member out from the user at least 1 inch, and preferably 2-5 inches, all along its length so that said at least one bias/tension preferably does not touch the user or the user's clothing. This feature of being distanced from the wearer's back (and preferably not touching the wearer at all), provides room for various amounts of adjustment of the bias/tension member in the upper bracket assembly. The distancing of the bias/tension member from the wearer allows room for attachment of the member to, and bending of the member between, the upper and lower brackets without rubbing or uncomfortable pressure.

Note that the preferred at least one bias/tension member provided in the apparatus is unattached to any other structure along substantially its entire length, except for its attachment or contact with the lower bracket or upper bracket. The preferred at least one bias/tension is distanced from the user's back and clothing preferably all along its length. The at least one bias/tension member is preferably not received inside said waist belt and is not considered a part of the waist belt or a rib or reinforcement of the waist belt. The preferred bias member(s) is not attached to said waist belt all along the length of the bias member(s). The apparatus preferably contains no rigid or semi-rigid horizontal bars. The preferred bias/tension member(s) are not segmented or jointed, do not telescope, and, instead, preferably are continuous. There are preferably no large plates in the apparatus, that is, especially none that covers a majority of the user's back, chest, or sides.

The preferred apparatus may be said to consist essentially of, or consist entirely of, a waist belt system and a chest belt system, with a leg strap system anchoring the waist belt, at least one spring-like member (preferably two), such as a tension rod or other elongated biasing member that is fixable at or near one end to the waist belt and slidably connected at or near its other end to a bracket near an upper region of the user's back. The elongated bias/tension member tends to straighten itself, and so, when the user bends over and exerts forces that tend to bend the bias member, the bias/tension member helps suspend or support the user in the bent-over position. The elongated bias member also, therefore, helps raise the user when he/she desires to stand up straight. The limited coverage of the user's body by the preferred apparatus, the relative lack of compression around the torso compared to many braces of the prior art, and the suspension of the user's upper body from the resilient biasing member, all help provide a light weight, comfortable, and un-encumbering back brace that provides force to the upper body, back, and spine when most needed, that is, when the user is bending over and/or lifting something. For example, the waist belt may be less than 8 inches wide from top to bottom (preferably 2-5 inches) and may not contact or compress the user's upper chest or upper back area. The waist belt need not be tight on the user (certainly not to the extent that it is uncomfortable); the leg strap system works to keep the waist belt rear region and the lower bracket assembly from tilting/pivoting, so that "cinching" the waist belt to try to accomplish this is not necessary. The user's back/spine is preferably not immobilized, but is rather supported and/or suspended, especially in any direction that tends to bend the biasing member, including the user bending over forward, but also preferably including bending to the side.

Instead of, or in addition to, being slidably connected to the chest assembly/upper bracket assembly, the at least one elongated bias member may be slidably received in the lower bracket assembly, or otherwise longitudinally (axially) slidably connected to the waist belt assembly. In order to increase the circumferential distance apart of the upper and lower bracket assemblies (as the user bends over, curving the at least one bias member on a radius), one or both ends of said at least one bias member may be slidably connected to the upper body (via the chest assembly) and to the waist (via waist belt assembly). However, it is important that said at least one bias member not be allowed to pivot during use relative to the upper and lower bracket assemblies (and hence not be allowed to pivot relative to the upper body and the waist) as this would allow the at least one bias member to not be tensioned/bent when the user bends over. It is also important that said at least one bias member not be allowed to slide completely out of the device during use, so some retention, stop, or other such safety means is necessary.

Bias members/tension rods may be various shapes, including rod-shaped, flat, hollow or solid, coiled or flat springs, or other shapes. Bias members/tension rods may be made of spring steel, fiber glass, graphite, or other resilient biasing material. Bias members/tensions rods may be of a type said to have a spring constant(s). Bias members/tension rods having different spring constants may be used for different user's body types, shapes, and preferences. Also, said spring constant may change along the length of the member/rod, for example, so that the performance of the member/rod may change as the user bends over to change the location at which the upper bracket contacts the member/rod to bend said member/rod. The tension rods illustrated in the Figures are a type of fiberglass construction such as might be useful in fishing poles and rods, but many other materials may be effective.

When two tension rods are used, which is preferred because they provide a centering effect, they may be installed to be about 1-4 inches apart, but other arrangements may be effective. Various lengths of bias members/tension rods may be used, for example, with the length preferably being sufficient to prevent them from sliding out of the tension rod tubes or other receiving bracket. While the brackets, belts, and straps portrayed in the Figures are preferred, many other styles may be effective. Leather, nylon, cotton, hyper-allergenic and/or anti-bacterial material, or other fabrics or materials may be used for the belts and straps. Upon viewing the preferred embodiments, it will be understood by one of skill in the art that other shapes, styles, and configurations may be effective.

Although this invention has been described above with reference to particular means, materials and embodiments, it is to be understood that the invention is not limited to these disclosed particulars, but extends instead to all equivalents within the broad scope of the following claims.

I claim:

1. A back support device comprising:
   a waist belt system and a chest strap system wherein the waist belt system comprises a lower posterior bracket, and the chest belt system comprises an upper posterior bracket comprising a back plate for resting against the back of the user and at least one tube connected to said back plate; and
   at least one elongated resilient bias member connected to the lower posterior bracket and slidably connected near it upper end to the upper posterior bracket, said at least one bias member being slidably received in said at least one tube so that the longitudinal axis of said at least one tube is parallel to the longitudinal axis of said at least one bias member;
   wherein said at least one tube is adjustable relative to the back plate so that the axis of said at least one tube and the axis of said at least one bias member are adjusted to various angles relative to the back plate;
   so that, when a user bends over to a bent-over position, the at least one resilient bias member slides in said upper posterior bracket and bends to provide force that helps support the user in the bent-over position and that assists the user in straightening up.

2. A back support device as in claim 1, wherein the at least one bias member comprises two tension rods.

3. A back support device as in claim 2, wherein said tension rods are parallel to each other.

4. A back support device as in claim 1, further comprising a leg strap system comprising at least one leg belt connected to a rear portion of the waist belt and adapted to encircle the user's leg to keep said rear portion of the waist belt from tilting relative to the user's body when the user bends over.

5. A back support device as in claim 1, comprising a connection between said lower posterior bracket and said at least one bias member that is adjustable for adjusting the length of the at least one bias member extending out from the lower posterior bracket.

6. A back support device as in claim 1, comprising an adjustable fixed connection between said lower posterior bracket and said at least one bias member, wherein the at least one bias member may be fixed to the lower posterior bracket in a variety of locations so that the distance the bias member extends above the lower posterior bracket may be adjusted prior to the user using the device.

7. A back support device as in claim 1, comprising a connection between said upper posterior bracket and said at least one bias member that is adjustable to hold said at least one bias member near its upper end in various positions relative to the upper posterior bracket, to accommodate various user body shapes and postures.

8. A back support device as in claim 1, wherein said upper posterior bracket is configured to hold said at least one bias member out from the user at least 1 inch all along its length so that said at least one bias member does not touch the user.

9. A back support device as in claim 1, wherein said at least one bias member is not received inside said waist belt.

10. A back support device as in claim 1, wherein said at least one bias member is not attached to said waist belt all along the entire length of the at least one bias member.

11. A back support device as in claim 1, wherein said at least one bias member comprises two cylindrical rods.

12. A back support device as in claim 1, wherein said at least one bias member is selected from a group consisting of a rod, a flat member, a hollow member, a solid member, a coiled spring, a flat spring, a spring steel member, a fiber glass member, and a graphite member.

13. A back support device comprising:
    a waist belt system, a chest strap system, and a leg strap system connected to the waist belt;
    the waist belt system comprising a waist belt and a lower posterior bracket having a front portion attached to the waist belt and a rear portion extending rearward from the waist belt;
    the chest belt system comprising an upper posterior bracket comprising a front portion comprising a plate for resting against the user's back and a rear portion comprising at least one tube; and
    a biasing system adapted to urge the user's upper body to remain in an upright position so that said biasing system supports said user's upper body against gravity when a user bends over;
    wherein said biasing system consists essentially of one or more resilient members connected to, and extending between, said rear portion of the lower posterior bracket and said rear portion of the upper posterior bracket so that the one or more resilient members are spaced from the user's back, each of said one or more resilient members having a longitudinal axis; and
    wherein said one or more resilient members are received, and longitudinally-slidable, in said at least one tube of the upper posterior bracket, and said at least one tube is adjustable relative to said plate, so that the longitudinal axis of said one or more resilient members is adjustable to various angles relative to the plate, wherein, when a user bends over to a bent-over position, said one or more resilient members slide in said at least one tube and bend to provide force that helps support the user in the bent-over position and that assists the user in straightening up.

14. A back support device as in claim 13, wherein the one or more resilient members each are slideable in said upper posterior bracket and are each bendable between said lower posterior bracket and said upper posterior bracket.

15. A back support device as in claim 13, wherein the waist belt is less than 8 inches wide from top to bottom and does not contact or compress the user's upper chest or upper back area.

16. A back support device as in claim 13, wherein said leg strap system provides downward tension on the waist belt to prevent a rear region of the waist belt from pivoting relative to the user's body.

17. A back support device as in claim 13, wherein said lower posterior bracket has multiple connection points for connecting to said one or more resilient members so that said one or more resilient members are adjustable in the distance said one or more resilient members extend from the lower posterior bracket.

18. A back support device as in claim 13, comprising a connection between said lower posterior bracket that is adjustable to adjust the distance said one or more resilient members extend from the lower posterior bracket.

19. A back support device as in claim 13, wherein said one or more resilient members are slidably connected to said lower posterior bracket.

20. A back support device as in claim 13, wherein said one or more resilient members are one or more resilient cylindrical rods.

21. A back support device as in claim 13, where said one or more resilient members are selected from a group consisting of a rod, a flat member, a hollow member, a solid member, a coiled spring, a flat spring, a spring steel member, a fiber glass member, and a graphite member.

* * * * *